United States Patent
Gross et al.

(10) Patent No.: US 6,541,628 B1
(45) Date of Patent: Apr. 1, 2003

(54) PROCESS FOR THE PREPARATION OF CORROLES AND SEVERAL SUCH NEW COMPOUNDS, INCLUDING CHIRAL DERIVATIVES, AND THE USE THEREOF

(75) Inventors: Zeev Gross, 1 Hibner Street, 49400 Petach Tikva (IL); Liliya Simkhovich, 12/16 Yoseftal Street, 26290 Kiryat Motzkin (IL); Nitsa Galili-Nachshon, Geva (IL); Irina Saltsman, 41/2 Hillel Street, 33071 Haifa (IL)

(73) Assignees: Technion Research and Development Foundation Ltd., Haifa (IL); Zeev Gross, Petach Tikva (IL); Liliya Simkhovich, Kiryat Motzkin (IL); Nitsa Gallili-Nachson, Geva (IL); Irina Saltsman, Haifa (IL)

( * ) Notice: Subject to any disclaimer, the term of this patent is extended or adjusted under 35 U.S.C. 154(b) by 0 days.

(21) Appl. No.: 09/787,885
(22) PCT Filed: Sep. 15, 1999
(86) PCT No.: PCT/IL99/00501
§ 371 (c)(1),
(2), (4) Date: Jun. 19, 2001
(87) PCT Pub. No.: WO00/18771
PCT Pub. Date: Apr. 6, 2000

(30) Foreign Application Priority Data

Sep. 29, 1998 (IL) .................................................. 126426

(51) Int. Cl.$^7$ ........................................... C07D 487/22
(52) U.S. Cl. ...................................... 540/145; 540/471
(58) Field of Search .................................. 540/471, 145

(56) References Cited

FOREIGN PATENT DOCUMENTS

WO    WO 96 08311 A1    3/1996

OTHER PUBLICATIONS

Neya et al. (Tetrahedron Letters, vol. 38, No. 23, pp. 4113–4116, 1997).*
Sessler, J.L.; Weghorn, S. J. Expanded, Contracted, & Isomeric Porphyrins, Pergamon, Oxford, 1997, pp. 11–83.
Vogel, E. J., "Novel Porphyrinoid Macrocycles and their Metal Complexes", Chem. 1996, pp. 1461–1487.
Liccoccia, S. and Paolesse, R., "Metal Complexes of Corroles and Other Corrinoids", Structure and Bonding, vol. 84 pp. 71–87.
Neya, Saburo, Ohyama, Kaori and Funasaki, Noriaki; "An Improved Synthesis of Corrole", Tetrahedron Letters, vol. 38, No. 23, 1997 pp. 4113–4116.
Rose et al., "Synthesis of biomimetic heme precursors", J. Am. Chem. Soc. vol. 118, No. 6, 1996, pp. 1567.
Chemical Abstracts, vol. 122, No. 10, Apr. 1995.
Chemical Abstracts, vol. 76, No. 13, Mar. 27, 1972.
Neya et al., "An improved synthesis of corrole", Tetrahedron Letters, vol. 38, No. 23, 1997 pp. 4113–4116.
Chemical Abstracts, vol. 127, No. 14, Oct. 1997.
Gross et al., "The first direct synthesis of corroles from pyrrole" Angew. Chem Int. Ed., vol. 38, No. 10, 1999, pp. 1427–1429.
Chemical Abstracts, vol. 92, No. 17, Apr. 1980.
Chemical Abstracts, vol. 127, No. 12, Sep. 22, 1997.
Paolesse et al., "5, 10, 15–Triphenylcorolle: A product from a modified Rothemund reaction", Chem Comm. Jul. 6, 1999, pp. 1307–1308.
Gross, et al., "N–Substituted Corroles: A Novel Class of Chiral Ligands", Angew. Chem. Int. Ed., vol. 38, No. 16, 1999.
Gross, et al., "Solvent–Free Condensation of Pyrrole and Pentafluorobenzaldehyde: A Novel Synthetic Pathway to Corrole and Oligopyrromethenes", Organic Letters, vol. 1, No. 4, 1999, 599–602.

* cited by examiner

*Primary Examiner*—Mukund J. Shah
*Assistant Examiner*—Kahsay Habte
(74) *Attorney, Agent, or Firm*—Oliff & Berridge, PLC

(57) ABSTRACT

A new process for the preparation of corroles, having the structure of formula I below relies on a solvent-free condensation of an aldehyde with a pyrrole. Further disclosed are several new corroles, salts, optically active isomers and complexes thereof synthesized using the process.

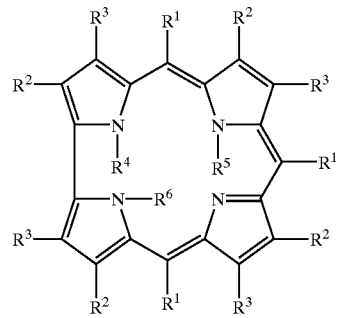

15 Claims, No Drawings

PROCESS FOR THE PREPARATION OF CORROLES AND SEVERAL SUCH NEW COMPOUNDS, INCLUDING CHIRAL DERIVATIVES, AND THE USE THEREOF

FIELD OF THE INVENTION

The present invention relates to a new process for the preparation of corroles and to a new class of corroles. The new class of corroles includes inter alia, water-soluble corroles and chiral corroles.

BACKGROUND OF THE INVENTION

The simplest corrole has the following structure:

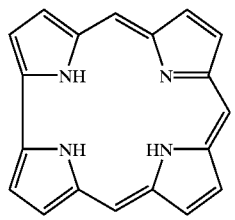

As shown in the above formula, corroles are slightly contracted porphyrins. Porphyrins are tetrapyrroles. They consist of four pyrrole rings (which are weakly aromatic) joined by methene bridges in a cyclic configuration, to which a variety of side chains are attached.

The metal complexes of porphyrin derivatives are involved in the most important biochemical processes, such as the binding and transportation of oxygen (the heme in myo- and hemoglobin), electron transfer (the heme in cytochromes), oxidation as part of biosynthesis and biodegradation (metabolism) of organic and inorganic compounds (heme-dependent enzymes), photosynthesis (magnesium chlorin in chlorophylls), and in Vitamin $B_{12}$ (cobalamin, with a reduced cobalt corrole structure). Synthetic metal complexes of porphyrins are extensively utilized as oxidation catalysts, as well as for other catalytic transformations. Also, a numerous number of porphyrins and their metal complexes are constantly tested for biomedical purposes, most notable for treatment of cancer and AIDS.

Corroles are much less known than porphyrins and their synthesis is a very complicated matter (a) Sessler, J. L.; Weghorn, S. J. in *Expanded, Contracted, & Isomeric Porphyrins*, Pergamon, Oxford, 1997, pp. 1–503. b) Vogel, E. *J. Heterocyc. Chem.* 1996, 33, 1461. c) Licoccia, S.; Paolesse, R. *Struct. Bond.* 1995, 84, 71). The first corrole was reported in 1965, and although the synthetic methods were improved during the years passed, there is still no simple procedure for that purpose. In this respect, even in the single and recently reported one-pot corrole synthesis (Ohyama, K.; Funasaki, N. *Tetrahedron. Lett.* 1997, 38, 4113), the dipyrrolic starting material is not commercially available and is also quite unstable. Because of the severe difficulties in the preparation of corroles, their potential in the fields where porphyrins were proven to be highly efficient was never explored.

OBJECTS OF THE INVENTION

It is an object of the present invention to provide a new and simple process for the preparation of corroles, starting from relatively simple and commercially available starting materials.

It is another object of the invention to provide novel corroles, their salts, optically active enantiomers and metal complexes thereof.

SUMMARY OF THE INVENTION

The synthetic approach relies on a one-pot, solvent-free condensation of an aldehyde with a pyrrole. All starting materials are commercially available and stable at ambient conditions (temperature, air, humidity) and the reaction yields are reasonable, considering the complexity of the products.

The term "solvent-free" refers to a reaction carried out without any solvent but may be performed with the aid of solid material, such as chromatographic supports or metal salts.

Thus, the present invention provides a process for the preparation of corroles of the following formula I:

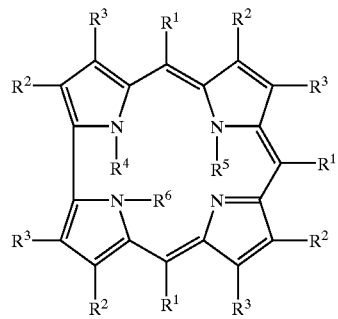

wherein:
each $R^1$ is hydrogen or is selected from straight or branched $C_1$–$C_{12}$ alkyl, aralkyl, aryl, heteroaryl, where any of these radicals may be substituted;

$R^2$ and $R^3$ are identical or different and each $R^2$ and each $R^3$ represents hydrogen or a radical selected from straight or branched $C_1$–$C_{12}$ alkyl, aralkyl, aryl, where any of these radicals may be substituted, and $R^4$, $R^5$ and $R^6$ are each hydrogen or represent identical or different radicals selected from straight or branched $C_1$–$C_{12}$ alkyl, aralkyl, aryl, acyl, alkylsulfonyl or arylsulfonyl. where any of these radicals may be substituted;

which process comprises solvent-free condensation of an aldehyde of formula II with a pyrrole of formula III

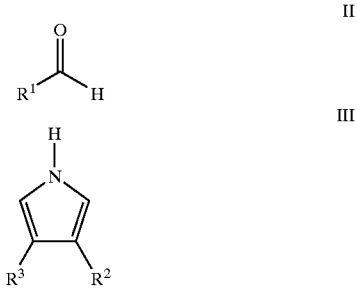

wherein $R^1$, $R^2$ and $R^3$ are as defined above, followed by dehydrogenation, to obtain a compound of formula I wherein $R^4$, $R^5$ and $R^6$ are hydrogen, and if desired converting said compound of formula I to a compound of formula I wherein at least one of $R^4$, $R^5$ or $R^6$ is other than hydrogen, and if desired converting any compound obtained into a salt or a metal complex.

Further disclosed are several new compounds of formula I, salts and metal complexes thereof. Also provided are optically pure enantiomers of these novel compounds. The metal complexes of the compounds of formula I were found to behave as very efficient catalysts in synthesis, for example in cyclopropanation or oxidation of hydrocarbons and in the alkylation of electrophilic derivatives. Some of the new corroles are easily converted into water-soluble derivatives, such feature being crucial for exploring certain potential applications.

DETAILED DESCRIPTION OF THE INVENTION

As stated above, one object of the present invention is to provide a new process for the preparation of corroles, the main advantages of which are listed below:

1. The synthetic procedure is a one-pot synthesis.
2. All starting materials are simple and commercially available.
3. The amount of chemicals, other than those which are absolutely required as the basic building blocks of the final material, is heavily reduced compared to all other known methods.

The new corroles which were prepared by the novel process described in this invention may be described by the general formula I:

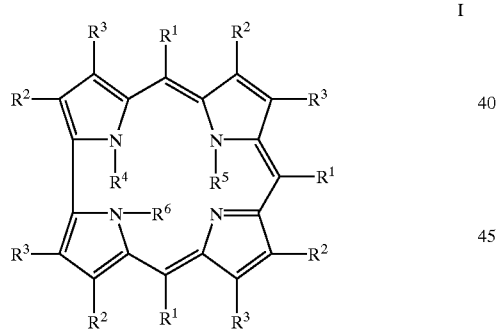

wherein each $R^1$ hydrogen or is selected from straight or branched $C_1$–$C_{12}$ alkyl, aralkyl, aryl, or heteroaryl, where any of these radicals may be substituted, $R^2$ and $R^3$ are each hydrogen, and $R^4$, $R^5$ and $R^6$ are each hydrogen, or one of them may represent a radical selected from straight or branched $C_1$–$C_{12}$ alkyl, aralkyl, aryl, carboxyl or sulfonyl, where any of these radicals may be substituted.

The $R^1$ group may have, for example the following meanings: 2,3,4,5,6-pentafluorophenyl; 2,6-difluorophenyl; 2,6-dichlorophenyl; 4-(2-pyridyl)-2,3,5,6-tetrafluorophenyl and 4-(N-methyl-2-pyridylium iodide)-2,3,5,6-tetrafluorophenyl. Several new corroles which were prepared by the process of the present invention are shown in the following formulae 1–9 in Scheme 1:

Scheme 1

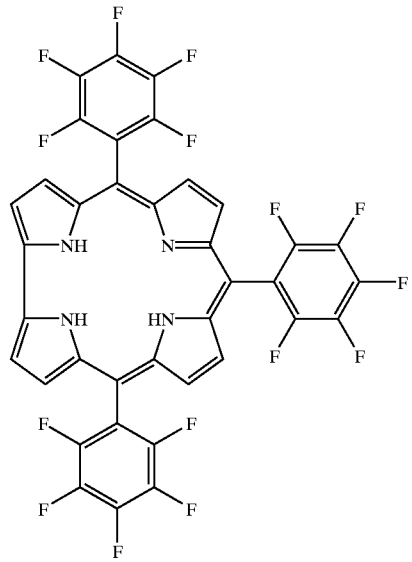

1

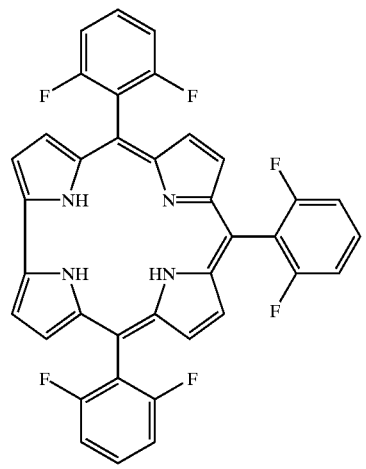

2

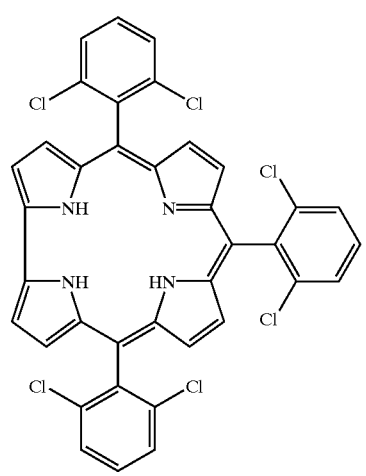

3

4
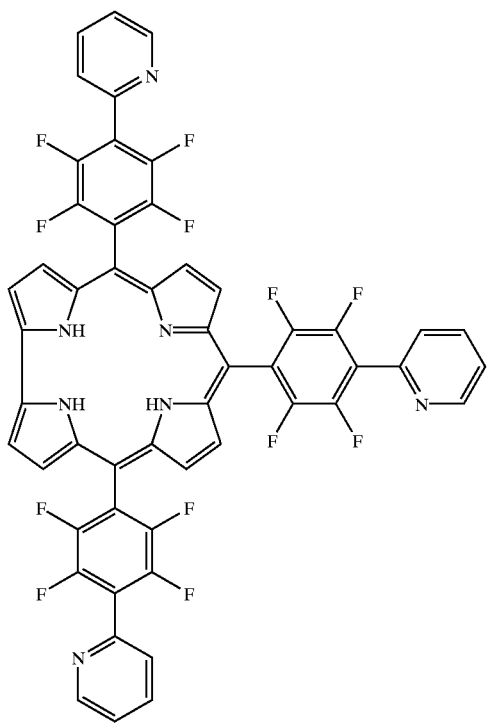
5
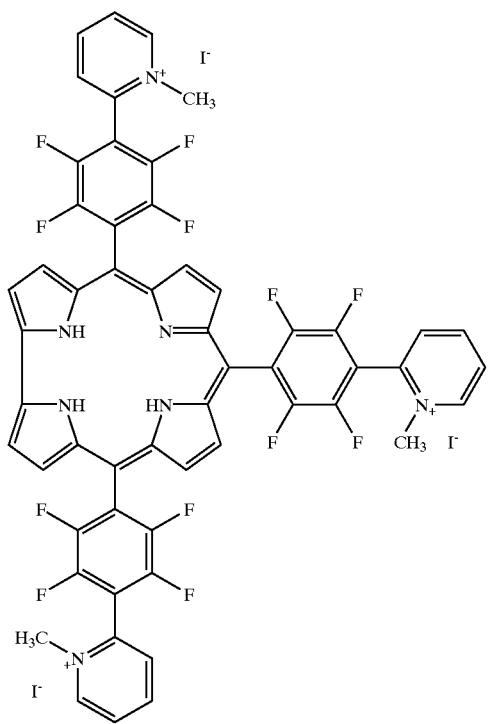
6
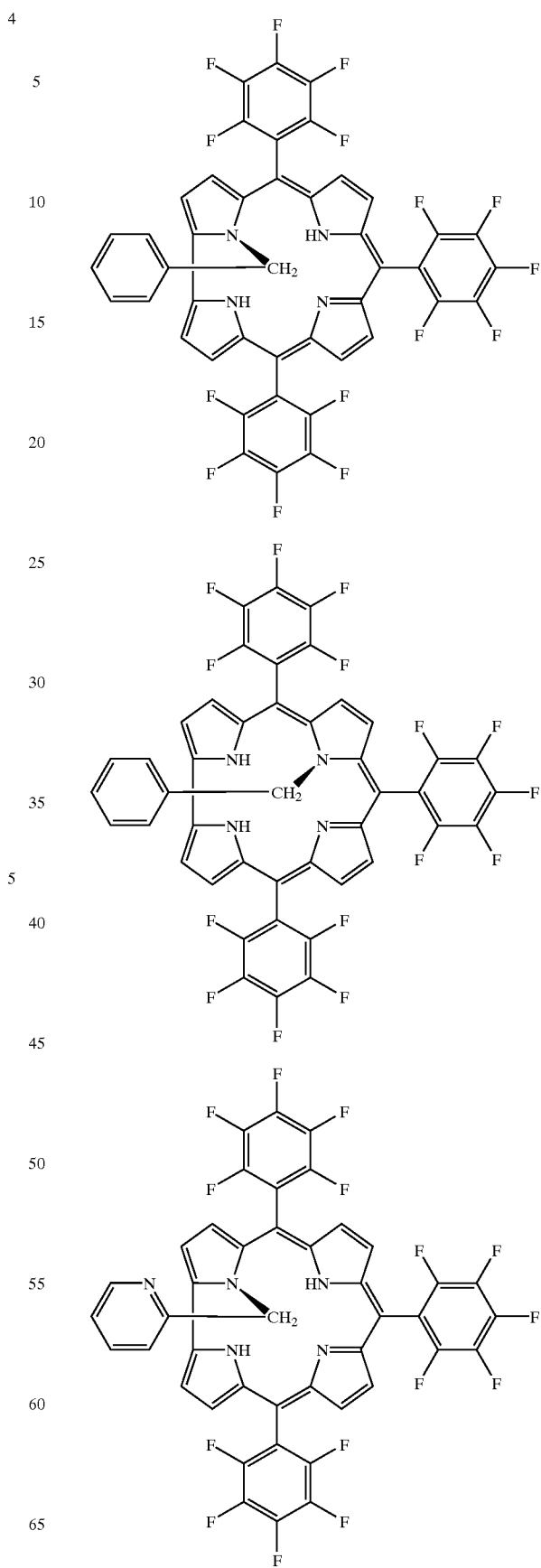
7
8

-continued

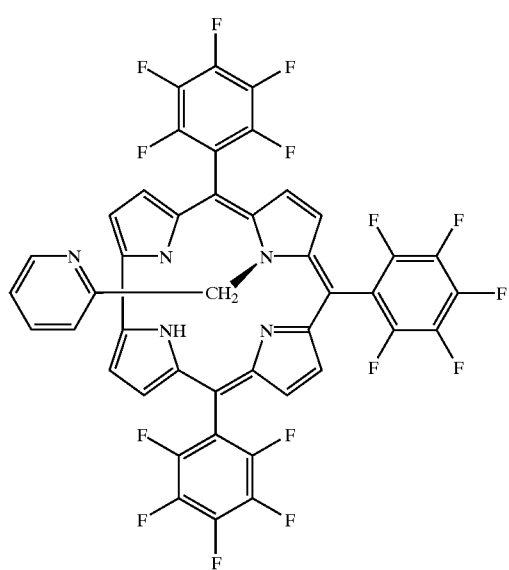

Other examples of new corroles according to the present invention are chiral corroles wherein one of the protons attached to the nitrogen in the pyrrole ring is replaced by a substituent, as for example an alkyl, alkylaryl, aryl, aralkyl, carboxy, or sulfuryl group. These chiral corroles may be represented by formulae IV and V as follows:

IV

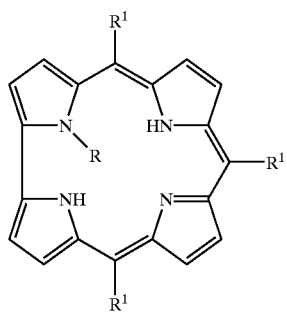

V

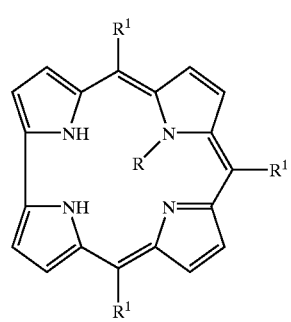

wherein $R^1$ is as defined above and R has the same meanings as given for either of $R^4$, $R^5$ and $R^6$ above. The structures shown in formulae IV and V represent the N(21)- and N(22)-substituted corroles, respectively. Both structures are chiral and can be resolved into enantiomers by crystallization in the presence of an enantiomerically pure acid.

The metal complexes of the corroles of formula I were found to behave as efficient catalysts. The structures of some novel metallocorroles according to the present invention are shown in Scheme 2 below:

Scheme 2
The structures of some new metallocorroles

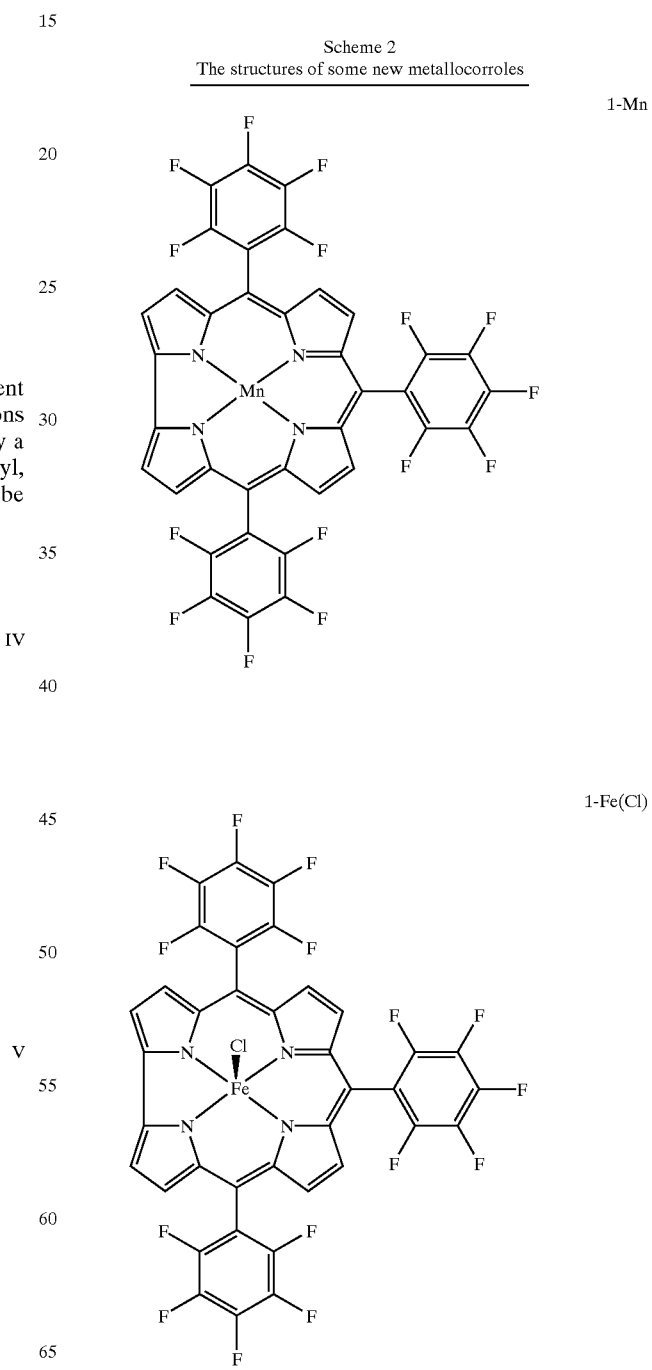

1-Co(PPh₃)
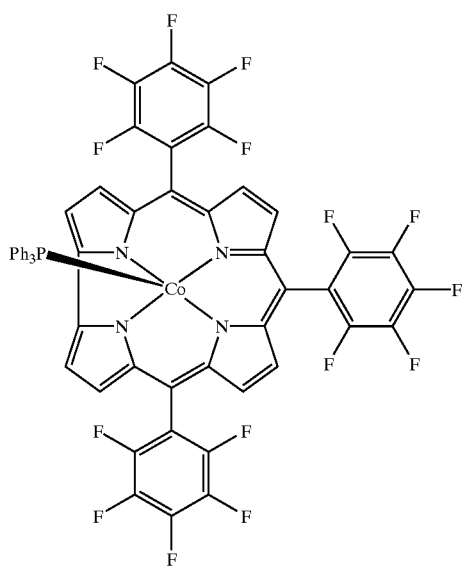
(1)₂(Fe)₂O
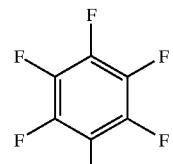
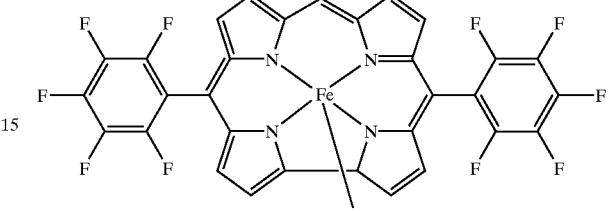
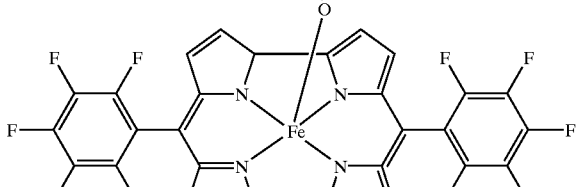
1-Cu
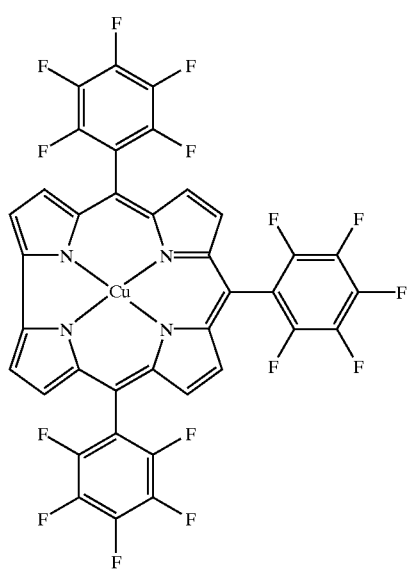
The following equations show potential uses of metallo-corroles as catalysts in organic synthesis, for example in epoxidation or cyclopropanation reactions:
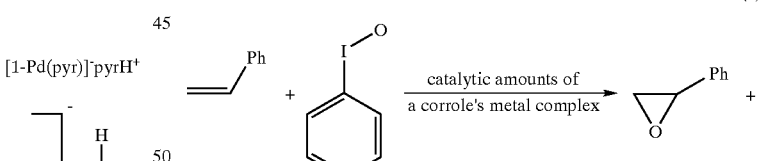 (1)
[1-Pd(pyr)]⁻pyrH⁺
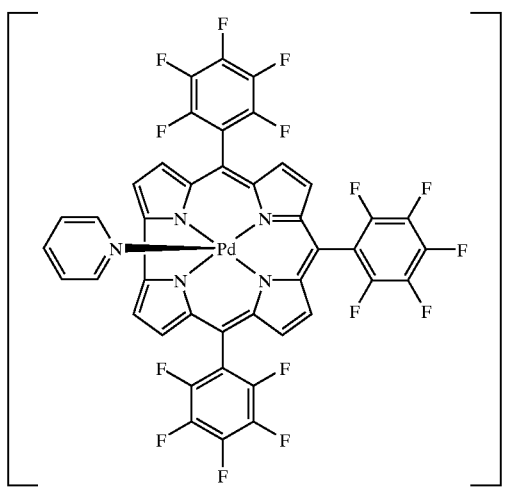
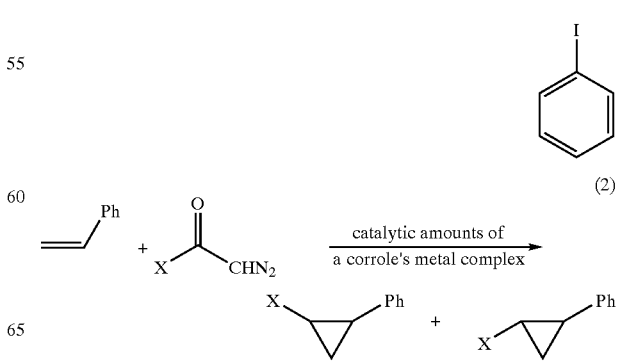 (2)

2a: X = a non chiral substituent,
such as EtO—

2b: X = a non chiral substituent,
such as:

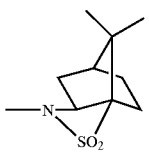

In reaction (2) above X might be either a non chiral substituent such as for example an EtO— group or a chiral substituent such as (+) or (−)2,10-camphorsultam.

The chiral corroles of the present invention, such as for example compounds 6–9 shown in Scheme 1 above, also exhibit catalytic effect on the addition of diethylzinc to aldehydes:

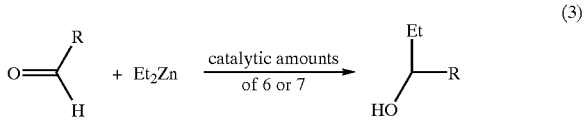

(3)

The substituent R may be a group selected from straight or branched $C_1$–$C_{12}$ alkyl, aralkyl, aryl, or heteroaryl.

The corroles of the present invention and the derivatives thereof such as metal complexes) have unique properties which are relevant to arious applications. Potential applications are in the fields of organic dyes and inks, non linear optics (NLO), conducting material, sensors (pH, ions, oxygen, etc.), conversion of solar energy to chemical and electrical energies.

The most potential applications of the corroles of the invention and their metal complexes are derived at least partially, from the following features:

1. The color of the corroles is highly sensitive to pH changes, as the neutral form is purple-red, while both the protonated (at pH<2) and the deprotonated forms (at pH>7) are intense-green.
2. A prerequisite for NLO and other applications which are based on molecules with a permanent dipole is the synthesis of asymmetrically substituted compounds. The advantage of the corroles in this context, is in view of the fact that their less symmetric structure (point symmetry of $C_{2v}$, like water) has an intrinsic polarity.
3. Properties as for example, conductivity, photoconductivity, photoluminescence, etc. are based on strong intermolecular interactions. The preliminary results with the iron and copper complexes of the corroles show that this interaction is stronger than in porphyrins. Thus, the corrole-corrole interactions in the $\mu$-oxo dimer $(1)_2(Fe)_2O$ shown in Scheme 2 are much stronger than in analogous porphyrin dimers.
4. The water-soluble derivatives of corroles, such as compound 5 shown in Scheme 1, undergo pH-dependent protonation and deprotonation processes in water.

The present invention will be described in more detail with the aid of the following non-limiting examples.

EXAMPLE 1

Preparation of 5,10,15-tris(2,3,4,5,6-pentafluorophenyl)corrole (1)

i) Solvent-free: from pyrrole and aldehyde

A solid absorbent (florisil, silica or alumina) (0.5 g) was mixed in a 50 mL flask with a 2 mL $CH_2Cl_2$ solution of 0.31 mL (2.5 mmol) of 2,3,4,5,6-pentafluorobenzaldehyde and 0.17 mL pyrrole (2.5 mmol), and the solvent was distilled at normal pressure. The condenser was removed and the solid mixture was heated to 100° C., upon which the color changed to black within 5–10 min. After heating for 4 h, the solid support was washed with 50 mL $CH_2Cl_2$, 0.25 g (1.1 mmol) DDQ was added, and the product was purified by chromatography on silica gel with hexane:$CH_2Cl_2$ (9:1) as eluent. The isolated chemical yield of 1 was 11%.

Compounds 5,10,15-tris(2,6-difluorophenyl)corrole (2) and 5,10,15-tris(2,6-dichlorophenyl)corrole (3) were prepared in a similar manner from the corresponding benzaldehydes, to give 6%, and 1% yields, respectively.

When the reaction between pyrrole and 2,3,4,5,6-pentafluorobenzaldehyde was carried out in the absence of any solid support but under the same reaction conditions and the same work-up procedure, compound (1) was formed and the yield was 5%. When the same reaction was performed at room temperature, the yield was 8–11%.

ii) In solution: from pyrrole, 2,2'bipyrrole, and aldehyde (in a ratio of 1:2:3)

A mixture of 2.5 mmol of 2,2'-bipyrrole (prepared in two steps from pyrrole and 2-pyrrolidinone in 30% yield. and freshly sublimed), 5 mmol of pyrrole and 7.5 mmol of the substituted benzaldehyde in 500 mL $CHCl_3$ was heated to reflux under a nitrogen atmosphere and 3.3 mmol of $BF_3$—$OEt_2$ was added. After 1 h, 7.5 mmol of DDQ were added and the reaction was heated for an additional 1 h. After cooling, 3.3 mmol of triethylamine was added and the solvent was evaporated. The isolated chemical yields of 1 and 3 after column chromatography were 3.3% and 2.2%, respectively.

1: UV-vis ($CH_2Cl_2$): $\lambda_{max}$ nm ($\epsilon \times 10^3$) 408 (114.0), 560 (17.6), 602 (9.3). $^1H$ NMR ($CDCl_3$): 9.10 (d, J=4.4 Hz, 2H), 8.75 (d, J=4.4 Hz, 2H), 8.57 (d, J=4.4 Hz, 4H), −2.25 (bs, 3H). $^{19}F$ NMR ($CDCl_3$): −137.55 (dd, $J^1$=24.2 Hz, $J^2$=8.1 Hz, 2F), −138.14 (dd, $J^1$=23.03 Hz, $J^2$=6.9 Hz, 4F), −152.52 (t, J=19.6 Hz, 2F), −153.10 (t, J=20.7 Hz, 1F), −161.78 (dt, $J^1$=24.2 Hz, $J^2$=8.1 Hz, 4F), −162.35 (dt, $J^1$=23.03 Hz, $J^2$=6.9 Hz, 2F). HRMS$^+$ (e/z) 797.085466, (calculated for $C_{37}H_{12}N_4F_{15}$: 797.082245).

2: UV-vis ($CH_2Cl_2$): $\lambda_{max}$ nm ($\epsilon \times 10^3$) 406 (118.6), 562 (20.3), 602 (11.9). $^1H$ NMR ($CDCl_3$): 8.99 (d, J=4.3 Hz, 2H), 8.71 (d, J=4.3 Hz, 2H), 8.52 (t, J=4.3 Hz, 4H), 7.72 (m, 3H), 7.33 (m, 6H), −2.1 (bs, 3H). $^{19}F$ NMR ($CDCl_3$): d −109.32 (t, J=6.4 Hz, 2F), −109.75 (t, J=6.4 Hz, 4F). HRMS$^+$ (e/z) 635.166000 (calculated for $C_{37}H_{21}N_4F_6$: 635.167041).

3: UV-vis ($CH_2Cl_2$): $\lambda_{max}$ nm ($\epsilon \times 10^3$) 408 (106.1), 422 (86.6), 560 (16.7), 604 (9.3). $^1H$ NMR ($CDCl_3$): 8.91 (d, J=4.2 Hz, 2H), 8.49 (d, J=4.8 Hz, 2H), 8.35 (d J=4.6 Hz, 4H), 7.72 (m, 3H), 7.33 (m, 6H), −1.7 (bs, 3H). MS$^+$ (e/z) 732.1 (MH$^+$, 100%), MS$^-$ (e/z) 730.7 ([M−H]$^-$, 100%). HRMS$^+$ (e/z) 729.981913 (calculated for $C_{37}H_{20}N_4Cl_6$: 729.981000)

EXAMPLE 2

Preparation of 5,10,15-tris(4-(2-pyridyl)-2,3,5,6-tetrafluorophenyl)corrole (4)

0.42 mL of an 1.6 M n-BuLi solution (0.7 mmol) was added to a stirred solution of 0.054 mL (0.56 mmol) 2-bromopyridine in 6 mL of dry THF under an argon atmosphere at −78° C., at such a rate that the temperature of the mixture did not exceed −70° C. After the addition was complete, the reaction mixture was stirred for 1 h at −78° C., to give a clear yellow solution. Next, a solution of 0.03 g (0.038 mmol) 5,10,15-tri(2,3,4,5,6-pentafluorophenyl) corrole (1) in 6 mL of dry THF was added dropwise. The mixture was stirred for 1 h at −78° C. and then hydrolyzed with saturated aqueous bicarbonate solution. The layers were separated, the aqueous layer washed with ether, and the combined ether extracts were dried and evaporated to a solid residue.

The product was purified by column chromatography on silica gel (1:1 EtOAc:Hexane) and recrystallized from $CH_2Cl_2$:Hexane to give 13 mg (35% yield) of the pure product as violet crystals.

UV-vis ($CH_2Cl_2$): $\lambda_{max}$ nm 414 (111.6), 564 (18.4), 606. $^1$H NMR ($CDCl_3$): 9.12 (d, J=3.9 Hz, 2H), 8.93 (m, 5H), 8.73 (d, J=4.88 Hz, 2H), 8.66 (d, J=3.91 Hz, 2H), 8.00 (dt, $J^1$=7.81 Hz, $J^2$=1.95 Hz, 3H), 7.84 (bd, J=7.81 Hz, 3H), 7.51 (dt, $J^1$=6.84 Hz, $J^2$=1.95 Hz, 3H), −2.02 (bs, 3H). $^{19}$F NMR ($CDCl_3$): −138.19 (q, J=23.79 Hz, 2F), −138.81 (q, J=23.79 Hz, 4F), −144.11 (q, J=23.79 Hz, 4F), −144.57 (q, J=23.79 Hz, 2F). MS$^+$ (e/z) 972.9 (MH$^+$, 100%), MS$^-$ (e/z) 972.7 ([M−H]$^-$, 100%).

EXAMPLE 3

Preparation of 5,10,15-tris(4-(N-methyl-2-pyridylium iodide)-2,3,5,6-tetrafluorophenyl)corrole (5)

A mixture of 11 mg (11 μmol) of 5,10,15-tri(4-(2-pyridyl)-2,3,5,6-tetrafluorophenyl)corrole (4) prepared in Example 2 and 0.8 mL(13 mmol) of $CH_3I$ in 2 mL of freshly distilled DMF was heated to 70° C. for 3 h. After evaporation of the solvent the product was recrystallized from MeOH:Ether to give 15.5 mg (98% yield) of the title compound as green solids.

UV-vis (MeOH): $\lambda_{max}$ nm ($\epsilon \times 10^3$) 430 (76.2), 576 (10.9), 622 (17.8). $^1$H NMR (DMSO-$d_6$): 9.49 (d, J=5.98 Hz, 3H), 9.16 (bm, 8H), 9.00 (t, J=8.54 Hz, 3H), 8.75 (t, J=7.68 Hz, 3H), 8.51 (t, J=7.68 Hz, 3H), 4.68 (s, 3H), 4.65 (s, 6H). $^{19}$F NMR (DMSO-$d_6$)): d −137.26(bm, 4F), −138.04 (bm, 6F), −138.60 (bm, 2F).

EXAMPLE 4

Preparation of N(21)-benzyl-5,10,15-tri(2,3,4,5,6-pentafluorophenyl)corrole (6) and N(22)-benzyl-5,10,15-tri(2,3,4,5,6-pentafluorophenyl)corrole (7)

A solution of 46 mg (58 μmol) 5,10,15-tri(2,3,4,5,6-pentafluorophenyl)corrole (1) in 30 ml of toluene was heated to reflux in the presence of 0.16 g dry $K_2CO_3$ while 5 mL of toluene was distilled out. After the solution reached RT, 70 μL (0.58 mmol) of benzylbromide was added at once and the mixture heated to reflux for 4 h. After evaporation of the solvent, the products were separated by column chromatography on basic alumina (100:2 Hexane:EtOAc). Two fractions were separated; 17 mg of 7 (33% yield, eluted first) and 21 mg of 6 (41% yield).

7: UV-vis ($CH_2Cl_2$): $\lambda_{max}$ nm 428(soret), 520, 560, 590, 648. $^1$H NMR ($CDCl_3$): 9.11 (t, J=4.28 Hz, 2H), 8.72 (d J=4.28 Hz, 1H), 8.64 (d J=4.28 Hz, 1H), 8.59 (bs, 1H), 8.44 (d J=5.35 Hz, 1H), 8.28 (d J=4.28 Hz, 1H), 7.96 (d J=5.35 Hz, 1H), 6.67 (t, J=7.5 Hz, 1H), 6.44 (t, J=7.5 Hz, 2H), 4.35 (d, J=7.5 Hz, 2H), −2.99 (bs, 2H), −3.48 (d, J=14.99 Hz, 1H), −4.09 (d, J=13.92 Hz, 1H). $^{19}$F NMR ($CDCl_3$): −137.43 (dt, $J^1$=24.87 Hz, $J^2$=9.04 Hz, 2F), −137.92 (dd, $J^1$=27.13 Hz, $J^2$=9.04 Hz, 1F), −138.6 (bt, J=27.13 Hz, 2F), −139.47 (bd, J=22.61 Hz, 1F), −152.22 (t, J=22.61 Hz, 1F), −152.64 (t, J=20.35 Hz, 1F), −153.10 (t, J=20.35 Hz, 1F), −161.9 (m, 6F). HRMS$^+$ (e/z) 887.123 (calculated for $C_{44}H_{18}N_4F_{15}$: 887.129196).

6: UV-vis ($CH_2Cl_2$): $\lambda_{max}$ nm 414(soret), 572, 612. $^1$H NMR ($CDCl_3$): 8.80 (dd, $J^1$=4.28 Hz, $J^2$=2.14 Hz, 1H), 8.72 (bd J=4.28 Hz, 1H), 8.59(m, 3H), 8.39(d J=4.28 Hz, 1H), 8.27 (d J=4.28 Hz, 1H), 7.60 (d J=4.28 Hz, 1H), 6.82 (t, J=7.5 Hz, 1H), 6.64 (t, J=7.5 Hz, 2H), 5.04 (d, J=7.5 Hz, 2H), −2.03 (d, J=13.92 Hz, 1H), −2.34 (d, J=14.99 Hz, 1H) −3.07 (bs, 2H). $^{19}$F NMR ($CDCl_3$): −137.15 (dd, $J^1$=27.6 Hz, $J^2$=10.2 Hz, 1F), −137.52 (dt, $J^1$=27.0 Hz, $J^2$=9.8 Hz, 2F), −137.95 (dd, $J^1$=27.6 Hz, $J^2$=9.8 Hz, 1F), −139.70 (d, J=22.8, 1F), −152.10 (t, J=22.0 Hz, 1F), −153.05 (t, J=22.4 Hz, 1F), −153.43 (t, J=22.0 Hz, 1F), −161.7 (m, 2F), −162.2 (m, 4F).

EXAMPLE 5

Preparation of N(21)-(2-pyridyl)-5,10,15-tris(2,3,4,5,6-pentafluorophenyl)corrole (8) and N(22)-(2-pyridyl)-5,10,15-tris(2,3,4,5,6-pentafluorophenyl) corrole (9)

These two compounds were prepared by essentially the same procedure as described in Example 4 above, but using 2-picolyl chloride hydrochloride instead of benzylbromide. 24 mg (72% yield) of (8) (eluted first) and 7.7 mg (23% yield) of (9) were obtained.

8: UV-vis ($CH_2Cl_2$): $\lambda_{max}$ nm 412 (soret), 572, 614. $^1$H NMR ($CDCl_3$): 8.84 (d, J=4.88 Hz, 1H), 8.64 (bs, 1H), 8.52 (m, 3H), 8.33 (d, J=4.88 Hz, 1H), 8.29 (d, J=4.88 Hz, 1H), 7.74 (d, J=4.88 Hz, 1H), 7.52 (d, J=3.66 Hz, 1H), 7.14 (t, J=7.32 Hz, 1H), 6.72 (t, J=7.32 Hz, 1H), 5.37 (d, J=7.32 Hz, 1H), −1.70 (d, J=15.87 Hz, 1H), −1.88 (d, J=15.87 Hz, 1H), −2.92(bs, 2H). $^{19}$F NMR ($CDCl_3$): −137.22 (m, 3F), −137.73 (d, J=22.61 Hz, 1F), −138.07 (d, $J^1$=22.61 Hz, $J^2$=9.04, 1F), −140.01 (d, J=22.61 Hz, 1F), −152.25 (t, J=22.61 Hz, 1F), −153.09 (t, J=22.61 Hz, 1F), −153.48 (t, J=22.61 Hz, 1F), −162.1 (m, 6F). MS$^+$ (e/z) 887.8, MS− (e/z) 885.6.

9: UV-vis ($CH_2Cl_2$): $\lambda_{max}$ nm 428 (soret), 518, 562,596, 650. $^1$H NMR ($CDCl_3$): 9.12 (t, J=4.66 Hz, 2H), 8.70 (d, J=4.66 Hz, 1H), 8.63 (d, J=4.66 Hz, 1H), 8.58 (d, J=4.66 Hz, 1H), 8.44 (d, J=4.66 Hz, 1H), 8.29 (d, J=4.66 Hz, 1H), 7.97 (d, J=4.66 Hz, 1H), 7.49 (d, J=5.59 Hz, 1H), 6.93 (dt, $J^1$=8.39 Hz, $J^2$=1.86 Hz, 1H), 6.56 (dt, $J^1$=5.59 Hz, $J^2$=2.80 Hz, 1H), 4.73 (d, J=7.45 Hz, 1H), −3.12 (bs, 2H), −3.28 (d, J=15.84 Hz, 1H), −3.94 (d, J=15.84 Hz, 1H). $^{19}$F NMR ($CDCl_3$): −137.56 (t, J=27.13 Hz, 3F), −138.64 (d, J=22.61 Hz, 1F), −138.88 (d, J=22.61 Hz, 1F), −139.72 (d, J=22.61 Hz, 1F), −152.23 (t, J=22.61 Hz, 1F), −152.68 (t, J=22.61 Hz, 1F), −153.24 (t, J=22.61 Hz, 1F), −161.9 (m, 6F); MS$^+$ (e/z) 887.8, MS− (e/z) 885.6.

EXAMPLE 6

Resolution of (7) into its Enantiomers

The addition of (1R)-(−)-10-camphorsulphonic acid to a $CH_2Cl_2$/hexane solution of the racemic N(22)-substituted corrole 7 resulted in a major thick crystalline form, together with some minute amounts of needle-like crystals. The solubility of the two crystalline forms in hexane was very different, practically none for the former and very high for the latter. Extensive washing of the solids with cold hexane afforded 6 in its enantiomerically pure form. The extent of resolution was judged by NMR investigation of $CDCl_3$ solutions of 6 in the presence of (1R)-(−)-10-camphorsulphonic acid, as well as in the presence of a chiral shift reagent.

EXAMPLE 7

Preparation of Metal Complexes of 5,10,15-tris-(2,3,4,5,6-pentafluorophenyl)corrole The following metal complexes of 5,10,15-tris(2,3,4,5,6-pentafluorophenyl)corrole have been prepared:

1. The Iron Complexes of Corrole 1: 1-Fe(Cl) and (1)$_2$(Fe)$_2$O

A mixture of 20 mg (25 μmol) of 5,10,15-tri(2,3,4,5,6-pentafluorophenyl)corrole (1) and 40 mg of FeCl$_2$ (0.3 mmol) in 5 mL of freshly distilled DMF was heated to reflux for 1 h. After evaporation of the solvent the mixture was dissolved in CH$_2$Cl$_2$ and washed with 10% HCl. The product was recrystallized from CH$_2$Cl$_2$:hexane to provide 18 mg (85% yield) of the (chloro)iron(IV) complex, 1-Fe(Cl).

1-Fe(Cl): UV-vis (CH$_2$Cl$_2$): $\lambda_{max}$ nm ($\epsilon$×10$^3$) 370 (42.1), 398 (46.1), 506, 606. $^1$H NMR (CDCl$_3$) (RT): −2.73 (bs, 2H), −11.3 (bs, 2H), −35.11 (bs, 2H). $^1$H NMR (CDCl$_3$) (260 K): 0.18 (bs, 2H), −4.82 (bs, 2H), −15.35 (bs, 2H), −44.24 (bs, 2H). $^{19}$F NMR (CDCl$_3$): −157.12 (bs, 2F), −160.77 (bs, 1F), −162.04 (bs, 2F), −164.38 (bs, 1F), −166.54 (bs, 4F), −166.94 (bs, 2F), −168.79 (bs, 1F), −169.43 (bs, 2F). HRMS$^+$ (e/z) 849.996 (calculated for C$_{37}$H$_9$N$_4$F$_{15}$Fe: 849.993709). MS$^+$ (e/z) 884.1, 848.8 (MH$^+$, 100%), MS$^-$ (e/z) 882.4, 847.5 ([M–H]$^-$, 100%).

The diamagnetic Woxo complex of corrole 1, (1)$_2$(Fe)$_2$O, was obtained in quantitative yield by repeated washing of a solution of 1-Fe(Cl) in CH$_2$Cl$_2$ by aqueous NaOH.

(1)$_2$(Fe)$_2$O: UV-vis (CH$_2$Cl$_2$): $\lambda_{max}$ nm 382 (soret), 544. $^1$H NMR (CDCl$_3$) (RT): 7.07 (d, J=4.04 Hz, 4H), 6.78 (d, J=4 Hz, 4H), 6.50 (d, J=5.14 Hz, 4H), 6.43 (d, J=5.14 Hz, 4H).

2. The Copper Complexes of Corrole 1: 1-Cu

A solution of 6 mg (7.5 μmol) of 5,10,15-tri(2,3,4,5,6-pentafluorophenyl)corrole (1) in 0.3 mL pyridine was warmed to 80° C. A solution of 4 mg (20 μmol) copper(II) acetate in 0.3 mL pyridine was also warmed to 80° C. and was added in one portion to the corrole solution. After 10 min at 80° C., the solvent was evaporated and the product was separated by column chromatography on silica gel (2:1 hexane:CH$_2$Cl$_2$), to provide 1-Cu in quantitative yield. 1-Cu exists as a Cu$^{III}$ corrole radical (broad NMR signals due to paramagnetism) at RT and as a Cu$^{III}$ corrole (sharp NMR signals, diamagnetic) at low temperatures.

1-Cu: UV-vis (CH$_2$Cl$_2$): $\lambda_{max}$ nm 404 (soret), 542. $^1$H NMR (CDCl$_3$) (RT): 7.95 (bs, 2H), 7.34 (bs, 2H), 6.99 (bs, 4H). $^1$H NMR (CDCl$_3$) (240 K): 7.94 (d, J=4.55 Hz, 2H), 7.49 (d, J=4.55 Hz, 2H), 7.18 (s, 4H). $^{19}$F NMR (CDCl$_3$): d −137.11 (d, J=17.8 Hz, 4F), −137.97 (d, J=17.4 Hz, 2F), −152.26 (dt, J$^1$=22.2 Hz, J$^2$=8.8 Hz, 3F), −160.91 (t, J=22.2 Hz, 6F).

3. The Manganese Complex of Corrole 1: 1-Mn

This complex was prepared by essentially the same procedure as described for 1-Fe(Cl), but using manganese(II) acetate tetrahydrate instead of FeCl$_2$. The product was obtained in quantitative yield. Recrystallization from EtOH/water afforded 1-Mn as a green solid.

1-Mn: MS (CI$^+$, isobutane) 848 ([M$^+$], 100%), 904 ([M$^+$+C$_4$H$_8$], 80%), 906 ([M$^+$+C$_4$H$_{10}$], 20%): UV-vis (CH$_2$Cl$_2$): $\lambda_{max}$ nm 398, 414 (Soret), 478, 596. $^1$H NMR (pyridine-d$_5$, RT): 21.0 (s, 2H), 19.0 (bs, 2H), −17 (bs, 2H), −42 (bs, 2H). $^{19}$F NMR (pyridine-d$_5$, RT): −117.5 (bs, 2F), −128.9 (bs, 4F), −152.3 (s, 1F), −154.2 (s, 2F), −158.1 (s, 2F), −159.0 (s, 4F). UV-vis (pyridine): $\lambda_{max}$ nm 396, 418, 432, 488, 600. $^1$H NMR (pyridine-d$_5$, RT): −4.0 (s, 2H), −19.0 (bs, 4H), −32.0 (bs, 2H). $^{19}$F NMR (pyridine-d$_5$, RT): −125.4 (bs, 4F), −139.0 (bs, 2F), −155.1 (s, 1F), −156.1 (s, 2F), −161.2 (s, 4F), −162.0 (s, 2F).

4. The Cobalt Complex of Corrole 1, 1-Co(PPh$_3$)

this complex was prepared in quantitative yields by succesive addition of 10.5 mg (13 μmol) 1, 10.8 mg NaOAc (130 μmol), 17.3 mg (67 μmol) PPh$_3$, and 16.4 mg (67 μmol) of Co(OAc)$_2$.4H$_2$O into 10 mL of ethanol, stiring at room temperature for 30 minutes, followed by evaporation of the solvent and flash-chromatography (CH$_2$Cl$_2$/hexanes).

1-Co(PPh$_3$): UV-vis (CH$_2$Cl$_2$): $\lambda_{max}$ nm 376, 408 (soret), 548, 584. $^1$H NMR (CDCl$_3$): 8.69 (d, J=4.4 Hz, 2H), 8.33 (d, J=4.8 Hz, 2H), 8.23 (d, J=4.8 Hz, 2H), 8.08 (d, J=4.6 Hz, 2H), 7.00 (td, J$^1$=7.7 Hz, J$^2$=1.9 Hz, 3H), 6.64 (td, J$^1$=8.0 Hz, J$^2$=2.2 Hz, 6H), 4.57 (dd, J$^1$=11.3 Hz, J$^2$=7.9 Hz, 6H). $^{19}$F NMR (CDCl$_3$): −137.16 (dd, J$^1$=24.6 Hz, J$^2$=8.1 Hz, 2F), −137.48 (dd, J$^1$=26.7 Hz, J$^2$=9.2 Hz, 1F), −138.49 (dd, J$^1$=24.3 Hz, J$^2$=8.3 Hz, 2F), −138.78 (dd, J$^1$=24.0 Hz, J$^2$=9.0 Hz, 1F), −154.07 (t, J=21.1 Hz, 3F), −162.0–−162.9 (m, 6F).

5. The Pyridinium Salt of the Pd(II) Complex of 1: [1-Pd(pyr)]$^-$pyrH$^+$

A solution of 6 mg (7.5 μmol) of 5,10,15-tri(2,3,4,5,6-pentafluorophenyl)cofrole (1) in 0.5 mL pyridine was treated with 1.9 mg (8.5 μmol) Palladium(II) acetate. The mixture was heated to 100° C. for 3 h and then hexane was slowly added until crystallization began. After filtration, 6.5 mg of the pyridinium salt of the palladium complex was obtained (95% yield).

UV-vis (CH$_2$Cl$_2$): $\lambda_{max}$ nm 380,412,440,550,584. $^1$H NMR (CDCl$_3$): 8.69 (d, J=5.59 Hz, 2H), 8.62 (d, J=4.12 Hz, 2H), 8.32 (d, J=4.11 Hz, 2H), 8.16 (d, J=4.34 Hz, 2H), 8.11 (d, J=3.97 Hz, 2H), 7.77 (t, J=7.47 Hz, 1H), 7.33 (t, J=6.71 Hz, 2H), 7.06 (bs, 1H), 5.99 (bs, 2H), 3.19 (bs, 2H). $^{19}$F NMR (CDCl$_3$): −136.6 (bm, 4F), −140.66 (bm, 2F), −154.94 (bm, 3F), −162.5 (bm, 4F), −164.05(bm, 2F).

EXAMPLE 8

Catalysis a) Epoxidation

1-Fe(Cl):Iodosylbenzene:Nitrobenzene:Styrene=1:100:100:1000.

0.32 mg (0.36 μmol): 8.5 mg (36 μmol): 3.7 mL (36 μmol): 41 mL (360 μmol)

The epoxidation was complete after 3.5 h, with a chemical yield of 87% (66% styrene oxide, 21% of phenyl acetaldehyde).

Similar results were obtained with 1-Mn as catalyst.

b) Hydroxylation

Ethylbenzene:Iodosylbenzene:1-Fe(Cl)=1000:100:1

61 μL (0.5 mmol), 11 mg (0.05 mmol), 0.5 mg (0.5 μmol), in 1 mL benzene.

The reaction was stirred overnight at RT, after which phenethyl alcohol and acetophenon were obtained in a 2.5:1 ratio, with a 20% yield. Similar results were obtained with 1-Mn as catalyst.

c) Cyclopropanation

1-Fe(Cl):EDA:Styrene=1:500:5000

1.3 mg (1.5 μmol): 78 μL (0.74 mmol): 0.85 μL (7.4 mmol)

The reaction was complete after 2 h and a 67 % yield of the cyclopropane products was obtained, with a trans :cis ratio of 2.18. Similar results were obtained with 1-Co(PPh$_3$) but with longer reaction times.

d) Asymmetric Cyclopropanation

1-Fe(Cl):enantiopure (+)-diazosultam (see equation 2):styrene=1:200:2000

0.6 mg (0.7 μmol): 40 mg (0.14 mmol): 0.16 mL (1.4 mmol)

The reaction was stopped after 27 h, when only traces of the diazo compound remained unreacted. The cyclopropane products were obtained in high yield with a trans:cis ratio of 1.2. The trans- and cis-isomers were obtained with 34% de (R,R) and 73% de (R,S), respectively.

e)Alkylation

To 2.2 mL solution of diethylzinc in hexane, 0.2 mL of benzaldehyde and 2 mg of a mixture of compounds 6 and 7 was added. After 17 h, the reaction was quenched by the addition of a few drops of saturated ammonium chloride. Solvent extraction (CH$_2$Cl$_2$/H$_2$O), followed by drying and evaporation of the organic solvent, and flash chromatography, resulted in the isolation of the addition product (1-phenyl-1-propanol) in 25% yield.

EXAMPLE 9

Synthesis of 5,10,15-tris(heptafluoropropyl)corrole 1.08 gr. (5 mmol) of heptafluorobutyraldehyde hydrate were mixed with 0.35 ml (5 mmol) of pyrrole, and heated to 65–70° C. for 3 hours. The brown oil was dissolved in CH$_2$Cl$_2$, and oxidized by 0.5 gr DDQ at room temperature. Chromatographic separation on silica-gel, followed by recrystallizations from CH$_2$Cl$_2$/hexane and from benzene/hexane, allowed the isolation of the pure 5,10,15-tris(heptafluoropropyl)corrole in about 1% yields.

TLC (Silica, CH$_2$Cl$_2$:n-hexane=1:2): R$_f$=0.75.

MS (DCI+, isobutane): 802.1 (M+, 100%), 782.2 (M+−HF, 20%), 764.1 (M+−2F, 17%).

UV-Vis (CH$_2$Cl$_2$, λ$_{max}$): 412 (e=116540), 510, 548, 610.

$^1$H-NMR (CDCl$_3$): 9.40 (4H), 9.24 (2H), 9.14 (2H).

$^{19}$F-NMR (CDCl$_3$, 188 MHz): −79.68 ppm (t, 9F, J=10.34 Hz), −83.28 (s, 2F), −96 (very broad s), −121.05 (s, 2F), −122.76 (s, 4F).

What is claimed is:

1. A process for the preparation of a compound of formula I or salts, optically active isomers and complexes thereof

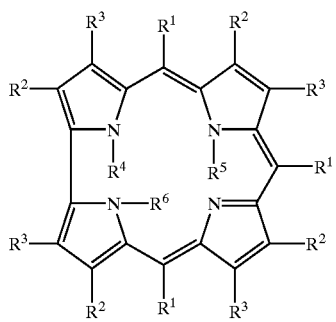

wherein:
each R$^1$ is a hydrogen or is selected from straight or branched C$_1$–C$_{12}$ alkyl, aralkyl, aryl and heteroaryl,
R$^2$ and R$^3$ are identical or different and each R$^2$ and each R$^3$ represents hydrogen or a radical selected from straight or branched C$_1$–C$_{12}$ alkyl, aralkyl and aryl, and
R$^4$, R$^5$ and R$^6$ are each hydrogen or represent identical or different radicals selected from straight or branched C$_1$–C$_{12}$ alkyl, aralkyl, aryl, acyl, alkylsulfonyl and arylsulfonyl;
which process comprises solvent-free condensation of an aldehyde of formula II with a pyrrole of formula III

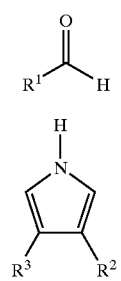

wherein R$^1$, R$^2$ and R$^3$ are as defined above, followed by dehydrogenation, to obtain a compound of formula I wherein R$^4$, R$^5$ and R$^6$ are hydrogen.

2. A process according to claim 1, wherein said condensation is carried out with heating.

3. A process according to claim 1, wherein said condensation is optionally carried out in the presence of a solid substrate.

4. A process according to claim 3, wherein said substrate is selected from silica, alumina and florisil.

5. A process according to claim 1, wherein a compound of formula I wherein R$^4$, R$^5$ and R$^6$ are each hydrogen is converted to a chiral compound of formula I wherein at least one of R$^4$, R$^5$ and R$^6$ is other than hydrogen.

6. A process according to claim 1, wherein R$^1$ is a group that forms either a positive or negative ion, so as to obtain a water-soluble compound of formula I.

7. A compound of formula I including the salts, the optically active isomers and the metal complexes thereof

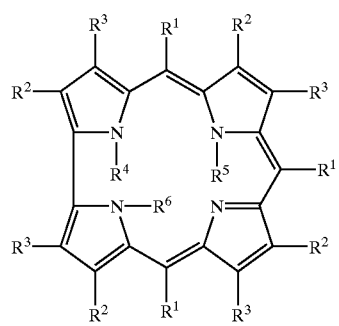

wherein
each R$^1$ is selected from straight or branched C$_1$–C$_{12}$ alkyl, aralkyl, aryl and heteroaryl,
R$^2$ and R$^3$ are each hydrogen, and
R$^4$, R$^5$ and R$^6$ are each hydrogen, or at least one of them may represent a radical selected from straight or branched C$_1$–C$_{12}$ alkyl, aralkyl, aryl, acyl, alkylsulfonyl and arylsulfonyl.

8. A compound of formula I in claim 7, wherein R$^1$ is an aryl group.

9. A compound of formula I in claim 7, wherein two of R$^4$, R$^5$ and R$^6$ represent hydrogen and the third represents straight or branched C$_1$–C$_{12}$ alkyl, aralkyl, aryl, carboxyl or sulfonyl, such a compound being in an enantiomerically pure form.

10. A metal complex of a compound of formula I in claim 7 including dimeric species thereof.

11. A catalyst comprising the metal complex according to claim 10.

12. The catalyst according to claim 11, wherein the catalyst catalyzes at least one of a cyclopropanation, an oxidation or an alkylation of hydrocarbons.

13. A process according to claim 2, wherein said condensation is optionally carried out in the presence of a solid substrate.

14. The process according to claim 1, wherein at least one of R$^4$, R$^5$ or R$^6$ of the compound of formula I is not hydrogen.

15. The process according to claim 1, wherein the compound of formula I is converted into a salt or metal complex.

* * * * *

UNITED STATES PATENT AND TRADEMARK OFFICE
CERTIFICATE OF CORRECTION

PATENT NO.    : 6,541,628 B1
DATED         : April 1, 2003
INVENTOR(S)   : Zeev Gross et al.

It is certified that error appears in the above-identified patent and that said Letters Patent is hereby corrected as shown below:

<u>Column 17,</u>
Line 39, that portion of claim 1 reading "$R^4$, $R^6$ and $R^6$" should read
-- $R^4$, $R^5$ and $R^6$ --.

Signed and Sealed this

Eighth Day of July, 2003

JAMES E. ROGAN
*Director of the United States Patent and Trademark Office*